US006944504B1

(12) United States Patent
Arndt et al.

(10) Patent No.: US 6,944,504 B1
(45) Date of Patent: Sep. 13, 2005

(54) MICROWAVE MEDICAL TREATMENT APPARATUS AND METHOD

(75) Inventors: G. Dickey Arndt, Friendswood, TX (US); Phong H. Ngo, Friendswood, TX (US); James R. Carl, Houston, TX (US); W. Raffoul George, Houston, TX (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 236 days.

(21) Appl. No.: 10/302,323

(22) Filed: Nov. 19, 2002

Related U.S. Application Data

(60) Continuation-in-part of application No. 09/746,533, filed on Dec. 18, 2000, now Pat. No. 6,675,050, which is a division of application No. 09/511,961, filed on Feb. 23, 2000, now Pat. No. 6,289,249.

(51) Int. Cl.$^7$ ................................................ A61F 2/00
(52) U.S. Cl. ....................... 607/101; 607/156; 607/154
(58) Field of Search ............................. 606/32–34, 41, 606/42, 48–50; 607/101, 102, 154, 156

(56) References Cited

U.S. PATENT DOCUMENTS

| 4,712,559 A | * | 12/1987 | Turner .......................... 607/99 |
| 4,860,752 A | * | 8/1989 | Turner .......................... 607/102 |
| 4,967,765 A | | 11/1990 | Turner et al. |
| 5,312,392 A | | 5/1994 | Hofstetter et al. |
| 5,366,490 A | | 11/1994 | Edwards et al. |
| 5,413,588 A | | 5/1995 | Rudie et al. |
| 5,464,437 A | | 11/1995 | Reid et al. |
| 5,509,929 A | | 4/1996 | Hascoet et al. |
| 5,575,811 A | | 11/1996 | Reid et al. |
| 5,599,294 A | * | 2/1997 | Edwards et al. ............... 604/22 |
| 5,620,480 A | * | 4/1997 | Rudie .......................... 607/101 |
| 5,643,335 A | | 7/1997 | Reid et al. |
| 5,720,718 A | | 2/1998 | Rosen et al. |
| 5,733,315 A | | 3/1998 | Burdette et al. |
| 5,755,754 A | | 5/1998 | Rudie et al. |
| 5,800,378 A | | 9/1998 | Edwards et al. |
| 5,800,486 A | | 9/1998 | Thome et al. |
| 5,830,179 A | | 11/1998 | Mikus et al. |
| 5,843,021 A | * | 12/1998 | Edwards et al. ............... 604/22 |
| 5,843,026 A | | 12/1998 | Edwards et al. |
| 5,843,144 A | | 12/1998 | Rudie et al. |
| 5,904,709 A | | 5/1999 | Arndt et al. |
| 6,035,238 A | * | 3/2000 | Ingle et al. .................... 607/98 |
| 6,289,249 B1 | | 9/2001 | Arndt et al. |
| 6,312,427 B1 | * | 11/2001 | Berube et al. ................. 606/33 |

* cited by examiner

Primary Examiner—Michael Peffley
(74) Attorney, Agent, or Firm—Theodore U. Ro

(57) ABSTRACT

Methods, simulations, and apparatus are provided that may be utilized for medical treatments which are especially suitable for treatment of benign prostatic hyperplasia (BPH). In a preferred embodiment, a plurality of separate microwave antennas are utilized to heat prostatic tissue to promote necrosing of the prostatic tissue that relieves the pressure of the prostatic tissue against the urethra as the body reabsorbs the necrosed or dead tissue. By utilizing constructive and destructive interference of the microwave transmission, the energy can be deposited on the tissues to be necrosed while protecting other tissues such as the urethra. Saline injections to alter the conductivity of the tissues may also be used to further focus the energy deposits. A computer simulation is provided that can be used to predict the resulting temperature profile produced in the prostatic tissue. By changing the various control features of one or more catheters and the methods of applying microwave energy, a temperature profile can be predicted and produced that is similar to the temperature profile desired for the particular patient.

8 Claims, 7 Drawing Sheets

MICROWAVE MEDICAL TREATMENT APPARATUS AND METHOD

This application is a continuation-in-part of U.S. application Ser. No. 09/746,533 filed Dec. 18, 2000, now U.S. Pat. No. 6,675,050 which is a divisional of U.S. application Ser. No. 09/511,961, now U.S. Pat. No. 6,289,249, filed Feb. 23, 2000 and issued Sep. 11, 2001.

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 U.S.C. 2457).

BACKGROUND OF THE INVENTION

1. Field of the Invention

The present invention relates to apparatus, methods, and computer simulations for radiating energy into body tissue and, more particularly, to a separated array of antennas and methods operable for highly selective heating of biological tissue.

2. Background of the Invention

Microwaves and other techniques have been used to necrose malignant, benign, and other types of cells and tissues including glandular and stromal nodules characteristic of benign prostate hyperplasia. Exemplary means for selective heating of body tissues without damaging healthy tissue are taught in U.S. Pat. No. 5,904,709, to Arndt et al., and also U.S. Pat. No. 6,289,249, a parent to the present application and discussed below, which are hereby incorporated herein by reference.

Benign prostatic hypertrophy or hyperplasia (BPH) is one of the most common medical problems experienced by men over 50 years old. Urinary tract obstruction due to prostatic hyperplasia has been recognized since the earliest days of medicine. During healthy operation, the bladder is emptied by way of the urethra, a tube passing through the prostrate gland. The main function of the prostate is to supply fluid for sperm that has been collected in the seminal vesicles. The seminal vesicles are supplied by the vas deferens from the epididymis, a tightly coiled tube next to the testicle that provides for the storage, transmission, and maturation of sperm.

Hyperplastic enlargement of the prostate gland, or enlargement due to abnormal but benign multiplication of the cells thereof, often leads to compression of the urethra thereby resulting in obstruction of the urinary tract. Common symptoms that develop from this condition may include more frequent urination, decrease in urinary flow, nocturia, pain, and discomfort. The incidence of BPH in men over 50 years of age is approximately 50 percent and increases to over 75 percent in men over 80 years of age. Symptoms of urinary obstruction occur most frequently between the ages of 65 and 70 when approximately 65 percent of men in the age group have prostatic enlargement.

When treatment by drug therapy is not sufficiently effective, surgical procedures for treating BPH are available but have potential side effects. General surgical risks apply such as anesthesia related morbidity, hemorrhage, coagulopathies, pulmonary emboli, electrolyte imbalance, and the like. Other problems that may occur from surgical correction include cardiac complications, bladder perforation, incontinence, infection, urethral or bladder neck stricture, retention of prostatic chips, and infertility. Due to the problems of surgery, many or even most patients delay treatment. However, the delay of treatment may lead to other complications including obstructive lesion in the prostate, chronic infection, and the like. Therefore, it is unquestionable that a need exists for improved surgical or non-surgical methods for treating BPH.

U.S. Pat. No. 5,904,709, issued May 18, 1999, to Arndt et al., discloses a method and apparatus for propagating microwave energy into heart tissues to produce a desired temperature profile therein at tissue depths sufficient for thermally ablating arrhythmogenic cardiac tissue to treat ventricular tachycardia and other arrhythmias while preventing excessive heating of surrounding tissues, organs, and blood. A wide bandwidth double-disk antenna is effective for this purpose over a bandwidth of about six gigahertz. A computer simulation provides initial screening capabilities for an antenna such frequency, power level, and power application duration. The simulation also allows optimization of techniques for specific patients or conditions. In operation, microwave energy between about 1 Gigahertz and 12 Gigahertz is applied to the monopole microwave radiator having a surface wave limiter. A test setup provides physical testing of microwave radiators to determine the temperature profile created in actual heart tissue or ersatz heart tissue. Saline solution pumped over the heart tissue with a peristaltic pump simulates blood flow. Optical temperature sensors disposed at various tissue depths within the heart tissue detect the temperature profile without creating any electromagnetic interference. The method may be used to produce a desired temperature profile in other body tissues reachable by catheter such as tumors and the like.

U.S. Pat. No. 6,289,249 B1, issued Sep. 11, 2001, to Arndt et al., discloses methods, simulations, and apparatus that are highly suitable for treatment of benign prostatic hyperplasia (BPH). A catheter is disclosed that includes a small diameter disk loaded monopole antenna surrounded by fusion material having a high heat of fusion and a melting point preferably at or near body temperature. Microwaves from the antenna heat prostatic tissue to promote necrosing of the prostatic tissue that relieves the pressure of the prostatic tissue against the urethra as the body reabsorbs the necrosed or dead tissue. The fusion material keeps the urethra cool by means of the heat of fusion of the fusion material. This prevents damage to the urethra while the prostatic tissue is necrosed. A computer simulation is provided that can be used to predict the resulting temperature profile produced in the prostatic tissue. By changing the various control features of the catheter and method of applying microwave energy a temperature profile can be predicted and produced that is similar to the temperature profile desired for the particular patient.

More generally, the following patents disclose attempts to solve the above-discussed difficult problems and related problems.

U.S. Pat. No. 5,843,144, issued Dec. 1, 1998, to Rudie et al., discloses a method for treating an individual with diseased prostatic tissue, such as benign prostatic hyperplasia, including inserting a catheter into a urethra to position a microwave antenna located within the catheter adjacent a prostatic region of the urethra. A microwave antenna is then driven within a power range for applying microwave energy substantially continuously to prostatic tissue to heat the prostatic tissue surrounding the microwave antenna at a temperature and for a time period sufficient to cause necrosis of the prostatic tissue.

U.S. Pat. No. 5,843,026, issued Dec. 1, 1998, to Edwards et al., discloses a method and apparatus for delivering controlled heat to perform ablation to treat the benign prosthetic hypertrophy or hyperplasia (BPH). According to the method and the apparatus, the energy is transferred directly into the tissue mass which is to be treated in such a manner as to provide tissue ablation without damage to surrounding tissues. Automatic shut-off occurs when any one of a number of surrounding areas to include the urethra or surrounding mass or the adjacent organs exceed predetermined safe temperature limits. The constant application of the radio frequency energy over a maintained determined time provides a safe procedure which avoids electrosurgical and other invasive operations while providing fast relief to BPH with a short recovery time. The procedure may be accomplished in a doctor's office without the need for hospitalization or surgery.

U.S. Pat. No. 5,830,179, issued Nov. 3, 1998, to Mikus et al., discloses a stent system and method for use in the prostate gland. The stent is made of a shape memory alloy such as nitinol, and has a low temperature martensite state, with a martensite transition temperature below body temperature, and a high temperature austenite state, with an austenite transition temperature at or above body temperature, and a memorized shape in the high temperature austenite state which is a helical coil of diameter large enough to hold the prostatic urethra open. The stent is used to heat the prostate and is left in the prostatic urethra while the prostate heals. After the prostate is substantially healed, the stent is cooled to its martensite state and is easily removed from the urethra.

U.S. Pat. No. 5,800,486, issued Sep. 1, 1998, to Thome et al., discloses an intraurethral catheter which includes a microwave antenna and a cooling lumen structure substantially surrounding the antenna. A cooling balloon partially surrounds the cooling lumens on one side of the catheter adjacent the microwave antenna. The cooling balloon improves wall contact between the catheter and a wall of the urethra to improve cooling of the urethra. The cooling balloon communicates with the cooling lumen structure to permit circulation of cooling fluid through the cooling balloon.

U.S. Pat. No. 5,800,378, issued Sep. 1, 1998, to Edwards et al., discloses a medical probe device comprising a catheter having a stylet guide housing with one or more stylet ports in a side wall thereof and a stylet guide for directing a flexible stylet outward through the stylet port and through intervening tissue at a preselected, adjustable angle to a target tissue. The total catheter assembly includes a stylet guide lumen communicating with the stylet port and a stylet positioned in said stylet guide lumen for longitudinal movement from the port through intervening tissue to target tissue. The stylet can be an electrical conductor enclosed within a non-conductive layer, the electrical conductor being a radio frequency electrode. Preferably, the non-conductive layer is a sleeve which is axially moveable on the electrical conductor to expose a selected portion of the electrical conductor surface in the target tissue. The stylet can also be a microwave antenna. The catheter can include one or more inflatable balloons located adjacent to the stylet port for anchoring the catheter or dilation. Ultrasound transponders and temperature sensors can be attached to the probe end and/or stylet. The stylet guide can define a stylet path from an axial orientation in the catheter through a curved portion to a lateral orientation at the stylet port.

U.S. Pat. No. 5,755,754, issued May 26, 1998, to Rudie et al., discloses an intraurethral, Foley-type catheter shaft containing a microwave antenna capable of generating a cylindrically symmetrical thermal pattern, within which temperatures are capable of exceeding 45 C. The antenna, which is positioned within the shaft, is surrounded by means within the shaft for absorbing thermal energy conducted by the tissue and asymmetrically absorbing electromagnetic energy emitted by the antenna-a greater amount of electromagnetic energy being absorbed on one side of the shaft. This asymmetrical absorption alters the thermal pattern generated by the microwave antenna, making it cylindrically asymmetrical, which effectively focuses microwave thermal therapy toward undesirous benign tumorous tissue growth of a prostate anterior and lateral to the urethra, and away from healthy tissue posterior to the urethra.

U.S. Pat. No. 5,733,315, issued Mar. 31, 1998, to Burdette et al., discloses an apparatus for applying thermal therapy to a prostate gland, comprising a support tube having a longitudinal central passageway, a power lead channeled through the longitudinal central passageway and an ultrasound crystal disposed around at least part of the support tube. The ultrasound crystal is coupled to the power lead which provides the power to energize the ultrasound crystal and generate ultrasound energy providing thermal therapy to the prostate gland. The ultrasound crystal further includes inactivated portions for reducing ultrasound energy directed to the rectal wall of the patient. A sealant is disposed in contact with the ultrasound crystal allowing vibration necessary for efficient ultrasound energy radiation for the thermal therapy to the prostate gland.

U.S. Pat. No. 5,720,718, issued Feb. 24, 1998, to Rosen et al., discloses a medical probe device comprising a catheter having a stylet guide housing with at least one stylet port in a side thereof and stylet guide means for directing a flexible stylet outward through at least one stylet port and through intervening tissue to targeted tissue. The stylet comprises an electrical central conductor which is enclosed within an insulating or dielectric sleeve surrounded by a conductive layer terminated by an antenna to selectively deliver microwave or radio frequency energy to target tissue. One embodiment includes the electrical conductor being enclosed within a non-conductive sleeve which itself is enclosed within a conductive sleeve in a coaxial cable arrangement to form a microwave transmission line terminated by an antenna. Another embodiment includes a resistive element near the distal end of the stylet which couples the center electrode to an outer conductor to generate joulian heat as electromagnetic energy is applied, such as an RF signal.

U.S. Pat. No. 5,643,335, issued Jul. 1, 1997, to Reid et al., discloses a system for treatment of benign prostatic hyperplasia within intraprostatic tissue surrounding a urethra. The system includes an intraurethral catheter having an intraurethral catheter shaft. An antenna is located within the catheter shaft for delivering heat to the intraprostatic tissue surrounding the urethra. Coolant fluid is circulated through a chamber located between the catheter shaft and the urethral wall.

U.S. Pat. No. 5,620,480, issued Apr. 15, 1997, to Eric N. Rudie, discloses a method for treating an individual with benign prostate hyperplasia. The method includes inserting a catheter into a urethra so as to position an energy emitting element located within the catheter adjacent a prostatic region of the urethra. A fluid is circulated within the catheter until the fluid stabilizes at a prechilled temperature. An energy emitting element is then energized sufficient to heat prostatic tissue surrounding the energy emitting element.

U.S. Pat. No. 5,599,294, issued Feb. 4, 1997, to Edwards et al., discloses a medical probe device comprising a catheter having a stylet guide housing with one or more stylet ports in a side wall thereof and guide means for directing a flexible stylet outward through the stylet port and through intervening tissue at a preselected, adjustable angle to a target tissue. The stylet can be an electrical conductor enclosed within a non-conductive layer, the electrical conductor being a radio frequency electrode. Preferably, the non-conductive layer is a sleeve which is axially moveable on the electrical conductor to expose a selected portion of the electrical conductor surface in the target tissue. The stylet can also be a microwave antenna.

U.S. Pat. No. 5,575,811, issued Nov. 19, 1996, to Reid et al., discloses a system for treatment of benign prostatic hyperplasia within intraprostatic tissue surrounding a urethra. The system includes an intraurethral catheter having an intraurethral catheter shaft. An antenna is located within the catheter shaft for delivering heat to the intraprostatic tissue surrounding the urethra. Coolant fluid is circulated through a chamber located between the catheter shaft and the urethral wall.

U.S. Pat. No. 5,509,929, issued Apr. 23, 1996, to Hascoet et al., discloses a urethral probe having a front part and a rear part, and a microwave antenna connected to an external device for generating microwaves. The microwave antenna has its primary active heating part arranged in the urethral probe to be directed onto the prostatic tissue located at least at the level of the bladder neck in the working position. The urethral probe constitutes an essential element of a device for the therapeutic treatment of tissues by thermotherapy, more particularly tissues of the bladder of a human being.

U.S. Pat. No. 5,464,437, issued Nov. 7, 1995, to Reid et al., discloses a system for treatment of benign prostatic hyperplasia within intraprostatic tissue surrounding a urethra. The system includes an intraurethral catheter having an intraurethral catheter shaft. An antenna is located within the catheter shaft for delivering heat to the intraprostatic tissue surrounding the urethra. Coolant fluid is circulated through a chamber located between the catheter shaft and the urethral wall.

U.S. Pat. No. 5,413,588, issued May 9, 1995, to Rudie et al., discloses an intraurethral, Foley-type catheter shaft containing a microwave antenna capable of generating a cylindrically symmetrical thermal pattern, within which temperatures are capable of exceeding 45 C. The antenna, which is positioned within the shaft, is surrounded by means within the shaft for absorbing thermal energy conducted by the tissue and asymmetrically absorbing electromagnetic energy emitted by the antenna-a greater amount of electromagnetic energy being absorbed on one side of the shaft. This asymmetrical absorption alters the thermal pattern generated by the microwave antenna, making it cylindrically asymmetrical, which effectively focuses microwave thermal therapy toward undesirous benign tumorous tissue growth of a prostate anterior and lateral to the urethra, and away from healthy tissue posterior to the urethra.

U.S. Pat. No. 5,366,490, issued Nov. 22, 1994, to Edwards et al., discloses a medical probe device comprising a catheter having a stylet guide housing with one or more stylet ports in a side wall thereof and guide means for directing a flexible stylet outward through the stylet port and through intervening tissue at a preselected, adjustable angle to a target tissue. The stylet can also be a microwave antenna.

U.S. Pat. No. 5,312,392, issued May 17, 1994, to Hofstetter et al., discloses a method of treating benign prostatic hyperplasia employing the steps of inserting a diffusing light guide into a prostrate lobe and providing laser power to the diffusing light guide in order to necrose surrounding tissue. The diffusing light guide can be inserted into the central or lateral prostrate lobes by inserting a needle and a trocar transperineally into the middle of the lateral lobe, removing the trocar, inserting the diffusing light guide, and monitoring the position of the needle, trocar, and diffusing light guide using ultrasound. The diffusing light guide can also be inserted into the central or lateral prostate lobes transurethrally and positioned with the aid of a urethroscope.

U.S. Pat. No. 4,967,765, issued Nov. 6, 1990, to Turner et al., discloses a urethral inserted applicator for prostate hyperthermia including a multi-tube, balloon type catheter. The catheter includes first and second closed end fluid dry tubes, respectively, for a helical coil antenna type applicator, and a microwave type temperature sensor for measuring the temperature of the prostate tissue, and an open fluid receiving tube. A microwave generator supplies electromagnetic energy to the applicator. A comparator is connected to the temperature sensor and a temperature reference potentiometer for comparing the actual tissue temperature level with a desired temperature level and outputting control signals to the microwave generator for controlling the output to the applicator. The coil type applicator is an elongated coil having a tip end connected to the center conductor of a coaxial cable and an opposite end connected to the outer conductor of the coaxial cable. A sheet or sheath of insulation material covers the coil antenna for insulating the coil from the tissue and the thickness of the sheet may be varied to provide uniform tissue heating along the length of the coil. The balloon of the catheter engages the body's bladder to position the applicator properly during the treatment.

Except for the patents listed above to Arndt et. al, the above cited prior art does not provide an easily fabricated catheter that may be fabricated with variations useful for individual patients, a computer simulation to predict the effect of procedural techniques, and a relatively quick procedure that may be performed in minutes to necrose prostatic tissue while protecting healthy tissue. There is a strong need for treatment techniques that permit accurate pinpointing of heat application within millimeters to necrose selected prostatic tissue while protecting the urethra and other healthy structures. Those skilled in the art have long sought and will appreciate the present invention that addresses these and other problems.

SUMMARY OF THE INVENTION

The present invention provides procedures, apparatus, and computer simulations for radiating energy into body tissue that is especially effective for treating benign prostatic hyperplasia (BPH). A preferred embodiment of the present invention provides a separated microwave antenna system operable for producing a controllable heating profile in a tissue region. This embodiment may comprise one or more elements such as, for instance, a first microwave antenna positioned adjacent the tissue region and a second microwave antenna positioned adjacent the tissue region. The first microwave antenna and the second microwave antenna are spaced apart and are controllable to produce the desired heating profile by utilizing constructive and destructive interference of microwave transmissions from the first microwave antenna and the second microwave antenna. The procedure is quickly performed and is designed to prevent damage to healthy tissue such as the urethra and colon. Additional elements may comprise a first elongate flexible member secured to the first microwave antenna operable for positioning the first microwave antenna at a first location adjacent the tissue region and a second elongate flexible member secured to the second microwave antenna operable for positioning the second microwave antenna at a second location adjacent the tissue region.

The separated microwave antenna may further comprise a microwave antenna control operable for supplying microwave power to the first microwave antenna and the second microwave antenna at one or more selected frequencies. In a preferred embodiment, the microwave antenna control is operable for supplying microwave power of the same operating frequency to the first microwave antenna and the second microwave antenna. Preferably, the operating frequency has a wavelength substantially equal to or less than a distance between first microwave antenna and the second microwave antenna. The microwave antenna control is also preferably operable for producing a selectable phase difference of the microwave transmissions at the operating frequency between the first microwave antenna and the second microwave antenna.

The invention provides a method for producing a selected heating profile in a tissue region of a body which may comprise one or more steps such as, for instance, positioning a first microwave antenna adjacent the tissue region, positioning a second microwave antenna adjacent the tissue region, controlling the first microwave antenna and the second microwave antenna to produce a desired heating profile in the tissue region by utilizing constructive and destructive interference of microwave transmissions from the first microwave antenna and the second microwave antenna.

The method may further comprise inserting the first microwave antenna into a urethra of the body and inserting the second microwave antenna into a colon of the body such that at least a portion of a prostrate of the body is between the first microwave antenna and the second microwave antenna.

Other steps may comprise providing that the microwave transmissions from the first microwave antenna and the second microwave antenna are made at the same operating frequency and/or providing that a distance between the first microwave antenna and the second microwave antenna is equal to or less than one wavelength of the operating frequency and/or adjusting a phase difference between the first microwave antenna and the second microwave antenna to produce a desired heating profile in the tissue region.

In one embodiment, the method may further comprise varying the conductivity of the tissue region and/or providing that the operating frequency is between 600 megahertz and 4000 megahertz. and/or cooling tissue adjacent at least one of the microwave antennas.

In another embodiment, the method provides for selective thermal ablation of a tissue to be treated while limiting thermal damage to a protected tissue with steps such as, for instance, positioning at least two energy radiators adjacent to the tissue to be treated and the protected tissue and controlling energy radiation from the at least two energy radiators to produce a thermal profile such that constructive interference of the energy radiation produces a temperature increase in the tissue to be treated for thermal ablation thereof and destructive interference of the energy radiation limits thermal damage to the protected tissue. In one preferred embodiment, the first energy radiator may be positioned within the urethra and the second energy radiator may be positioned within the colon. The distance between the at least two energy radiators may be equal to or less than a wavelength of the operating frequency and/or frequency of operation may be selected based on a distance of the at least two energy radiators to the tissue to be treated.

Another embodiment of the method may comprise positioning a first microwave radiator directly adjacent a first protected tissue region, positioning a second microwave radiator directly adjacent a second protected tissue region, providing that the tissue to be treated is substantially between the first microwave radiator and the second microwave radiator, and controlling microwave radiation from the first microwave radiator and the second microwave radiator such that constructive interference of the microwave radiation occurs in the tissue to be treated to focus the heat energy therein and that destructive interference of the microwave radiation occurs in the first protected region and the second protected region to limit heat energy deposited therein.

A computer program for determining a temperature profile in a biological tissue due to microwave radiation may comprise providing position information for a plurality of microwave antennas with respect to each other and with respect to the biological tissue, providing at least one frequency of operation for the plurality of microwave antennas, and providing a phase difference of the microwave radiation for the plurality of microwave antennas. The computer program may further comprise providing a power level of operation of the plurality of microwave antennas, utilizing conductivity of the biological tissue and/or providing a delivery time of microwave energy and/or determining effects of cooling applied adjacent the plurality of antennas. The computer simulation may be used to predict a temperature profile that will be produced given the various inputs related thereto. Alternatively, it may be used to provide suitable procedure variables such as frequency, time duration, and power level, given the desired temperature profile. Alternatively, it may be utilized for controlling the antennas to produce the desired temperature profile.

Another embodiment of the method may comprise positioning one or more microwave radiators adjacent the biological tissue to be treated, adjusting a conductivity of the tissue to be treated by injecting solution into the biological tissue to produce conductivity adjusted tissue, and utilizing the one or more microwave radiators to transmit the microwave radiation into the conductivity adjusted tissue.

Yet another embodiment may comprise forming one or more holes in a prostrate, inserting at least one microwave antenna directly into the prostate tissue through the one or more holes, and radiating microwave energy into the prostate.

The method may further comprise injecting a solution for controlling a conductivity of the prostate tissue and/or positioning the at least one antenna directly adjacent tissue to be ablated.

The antenna may be made directional to protect structures such as the colon and structures such as ducts radially outside the urethra. For purposes of the present invention, a catheter is assumed to include a probe, cannula or other medical device for insertion into the body such as into the urethra for treatment purposes.

For this purpose, a separated microwave antenna system is disclosed that comprises one or more catheters preferably formed from a microwave transmission line having first and second opposing ends. The first end may be adapted for connection to a microwave power source. The microwave transmission line preferably has a center conductor and an outer conductor. A microwave antenna is disposed on the second end of the microwave antenna.

Electrical insulating material is preferably provided between the center conductor and the outer conductor. The microwave antennas may be disposed within the electrical insulating material, if desired.

One object of the present invention is to provide an improved instrument and method for necrosing certain tissue while protecting other tissue.

Another object of the present invention is to provide an improved instrument, method, and computer simulation for treating benign prostatic hyperplasia.

Yet another objective of the present invention is to provide a treatment that necroses prostatic tissue but protects other tissue such as the urethra.

Any listed objects, features, and advantages are not intended to limit the invention or claims in any conceivable manner but are intended merely to be informative of some of the objects, features, and advantages of the present invention. In fact, these and yet other objects, features, and advantages of the present invention will become apparent from the drawings, the descriptions given herein, and the appended claims.

While the present invention will be described in connection with presently preferred embodiments, it will be understood that it is not intended to limit the invention to those embodiments. On the contrary, it is intended to cover all alternatives, modifications, and equivalents included within the spirit of the invention and as defined in the appended claims.

BRIEF DESCRIPTION OF PREFERRED EMBODIMENTS

The present invention utilizes a separated antenna array to deliver microwave power radiation within a highly definable field of a selectable size and volume to necrose tissue. The techniques, catheters, and computer simulation of a preferred embodiment of the present invention provide means for achieving deep heating of tissue without the need for overly heating tissue directly surrounding the catheter as is particularly useful for treating benign prostatic hyperplasia without damaging healthy tissue, the urethra, or other adjacent organs. Computer simulations and laboratory testing using phantom material to represent the prostrate have shown that by selectively controlling parameters of the microwave radiators, e.g., the frequency and relative phasing of the microwave radiators, that tissue in the prostate can be necrosed in precise, selectable, regions that are controlled within a few millimeters.

Thus, a preferred embodiment of the present invention provides a separated array of microwave antennas for radiating energy into body tissue used to generate controlled regions of temperature increase high enough to thermally destroy areas within the prostate. The heated region can be controlled both in the desired temperature heating as well as the particular spatial area to be treated. Several variations in the microwave radiators (catheters) have been simulated and tested for treating specific locations as well as additional enhancements to focus the heating.

Figure 1:
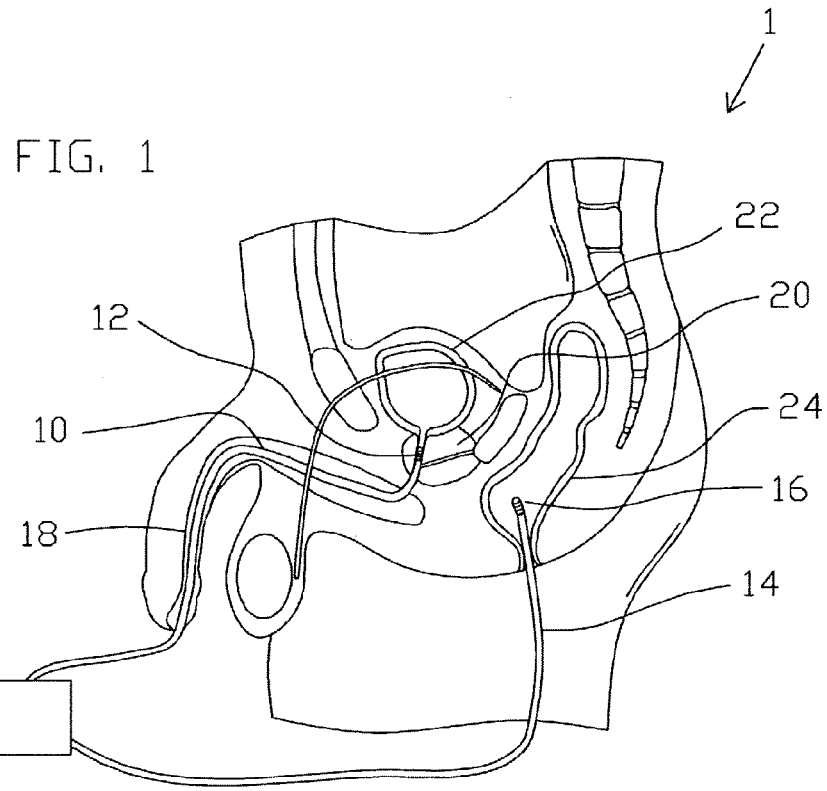
FIG. 1 is an elevational view, in section, of the male urinary and reproductive system showing a separated array of microwave antennas carried by catheters positioned to surround the prostrate in accord with a presently preferred embodiment of the invention.

Referring now to the drawings, and more particularly to FIG. 1, the present invention discloses a separated antenna array 1 in accord with the present invention comprising urethra catheter 10 with urethra antenna 12 and colon catheter 14 with colon antenna 16. Urethra catheter 10 and one or more urethra antennas 12 may extend through urethra 18 so as to be positioned in prostrate 20 adjacent bladder 22. One or more colon catheters 14 and colon antennas 16 are positioned at a selected position in colon 24 adjacent prostrate 20. The relative placement of microwave antennas 12 and 16 will be determined based on factors such as the selected prostrate tissue to be ablated, antenna pattern, distance between the antennas, frequencies, and related factors, as discussed in more detail hereinafter. Control 25 may be utilized to adjust frequencies, amplitudes, phase differences, provide impedance matching, control timing as per computer program control, and for other functions related to controlling microwave antennas 12 and 16.

In one presently preferred embodiment of the invention, microwave antennas 12 and 16, discussed hereinafter, would be disk loaded monopole antennas of proven design with good efficiency and low sensitivity to detuning due to heating as taught by one of the aforementioned patents such as U.S. Pat. No. 5,904,709, or U.S. Pat. No. 6,289,249, or patents related thereto, which are incorporated herein by reference. Because this antenna design has a very broad bandwidth, it can be used over a wide range of frequencies with little degradation in performance and is highly tolerant to manufacturing and operating environment variations.

In general, basic operation of a procedure for ablating prostatic tissue may first require determining the area or areas of the prostate to be heated. The next basic step may require positioning the microwave radiators or antennas 12 and 16 in urethra 18 and colon 24 to positions adjacent, if possible, the selected region(s) of prostrate tissue to be heated.

The relative distance between antennas 12 and 16, the frequencies of operation, and the relative phase may be used to control heat applied to a selected region. To illustrate one principle of operation, antennas 12 and 16 may operate at the same frequency and amplitude. A 180 degree phase shift may be utilized between urethra antenna 12 and a colon antenna 16 to thereby provide maximum (in-phase) addition of the two signals at a point one-half the distance between antennas 12 and 16. If the selected region to be heated is not exactly one-half the distance between antennas 12 and 16, then by varying the relative phase, the point of maximum heating (in-phase signal addition) can be varied as desired. As well, other factors such as frequency, position, and the like may be varied. The principle of operation is based upon constructive and destructive interference of microwaves and the resulting heating profile produced thereby. While the preferred modes of operation are discussed herein, in general the frequency, amplitude, and relative phase of two or more antennas may be adjusted to produce constructive and destructive wave interference thereby producing a controlled and desired heating profile.

EXAMPLE 1

Figure 2:
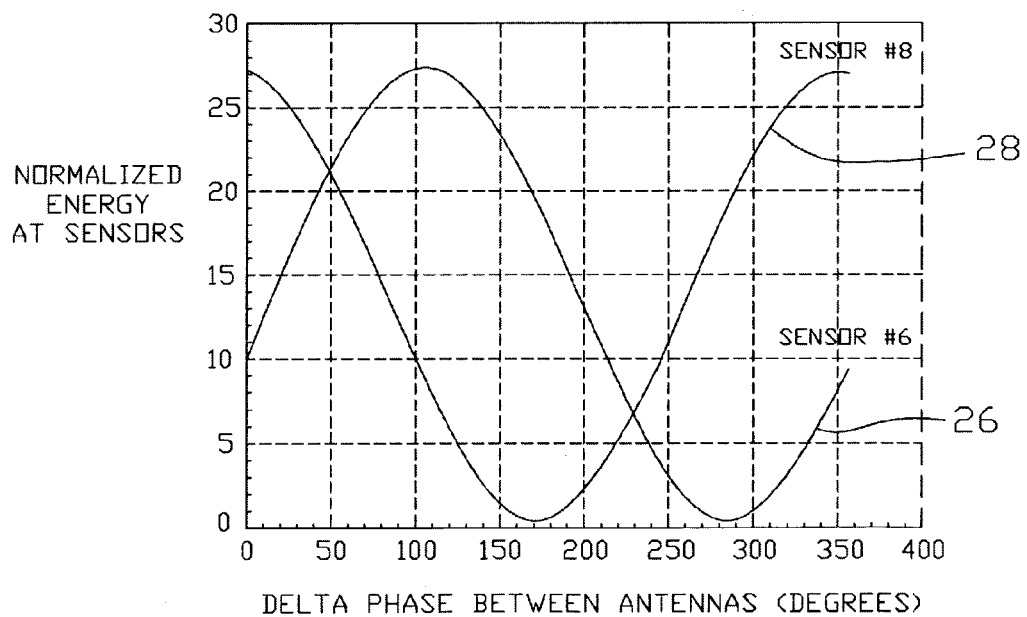
FIG. 2 is a graph of a computer simulation and/or laboratory test showing heating profiles of tissue at two temperature sensors spaced 3 millimeters apart with the energy received from two antennas spaced 3.8 centimeters apart as the phase relationship between the antennas is varied in accord with the present invention.

FIG. 2 shows computer projected results and/or laboratory testing results for a configuration whereby urethra antenna 12 and colon antenna 16 are separated by 3.8 centimeters and operating at 1.5 GHz. Numerous sensors may be utilized for laboratory testing and/or computer projections. In Example 1, sensor # 6 is located 20.5 mm from urethra antenna 12 and 14.5 mm from colon antenna 16. Sensor #8 is 23.5 mm from urethra antenna 12 and 11.5 mm from colon antenna 16. The spacing between sensors 6 and 8 is 3 mm. As can be seen in the data recorded in FIG. 2, the heating energy at each of the two sensor locations can vary from a maximum (the radiated energies from each antenna constructively add together in-phase) to a minimum (the radiated energies from each antenna destructively subtract from each other when 180 degrees out of phase) by simply adjusting the relative phase between antennas 12 and 16. The temperature variation at sensor 6 in response to changes in the phase difference between the antennas is shown by curve 26. Likewise, the temperature variation at sensor 8 in response to changes in the phase difference between the two antennas is shown by curve 28. For instance, looking at a delta phase of 150 degrees between antennas 12, it is demonstrated that even when the sensors are 3 mm apart, one sensor receives almost maximum energy while the other sensor receives almost no energy. Thus, the placement of energy in tissue is very precise. If the region to be heated extends over a relatively large distance, then the phase can be sequentially adjusted in steps or by sweeps, such as by computer control, as desired during the heating process such that sufficient heat to produce ablation occurs over the entire selected region.

In a presently preferred embodiment, the antennas are one wavelength apart because this has been found to provide an optimal heating profile. Various factors for this selection relate to the heating profiles produced by addition and subtraction of the signals, e.g., constructive and destructive interference, and other factors such as signal loss and the like. Other separation distances such as, for example, the heating profile when the antennas are one-half wavelength apart may not be as desirable for all applications. It will be noted that the speed of electromagnetic waves through the body is considerably slowed as compared to the speed in a vacuum so that the frequencies of operation to produce the desired wavelength are different than would be calculated in space. It is also noted that while a one wavelength separation distance between the antennas is a convenient and presently preferred antenna separation distance, other distances less than one wavelength could be utilized, if desired, whereby signals may also be added and subtracted. Separation distances significantly more than one wavelength may result in a periodic heating profile; however, these profiles may also be considerably affected by signal losses. Due to significant signal loss with increasing antenna separation distance, the addition and subtraction of signals may not produce sufficient heating at the desired locations, depending on the losses, distances, frequencies, and other factors. Thus, although other antenna separation distances could be utilized in accord with the present invention, a separation distance of one wavelength is found to be convenient and most applicable to typical operational conditions.

By adjustment of the frequency, phase, directionality, and duration of the microwave radiation and/or by cooling of the catheters (such as with fusion material or other means discussed in detail in one or more parent patent applications to this application) a wide variety of heat profiles in the prostate are possible. Various means may be provided to determine the distance between the antennas, including timing/reception/measurement of electromagnetic signals, or acoustic signals, so this information is readily available. As well, means may be provided, such as ultrasound means, x-rays, optical/laparoscopic means, or other means to verify positioning/orientation of antennas 12 and 16 with respect to the prostrate. While the present invention is described in terms of two antennas for easier understanding, it will be understood that more than two antennas may be used, if desired. Computer programs may be utilized to project the effect/benefit of a preferred separated antenna array with any number of antennas for heating any particular region of tissue. Additional antennas may be provided spaced apart along common catheters and/or additional catheters carrying additional antennas may be utilized where sufficient room is available.

EXAMPLE 2

Figure 7:
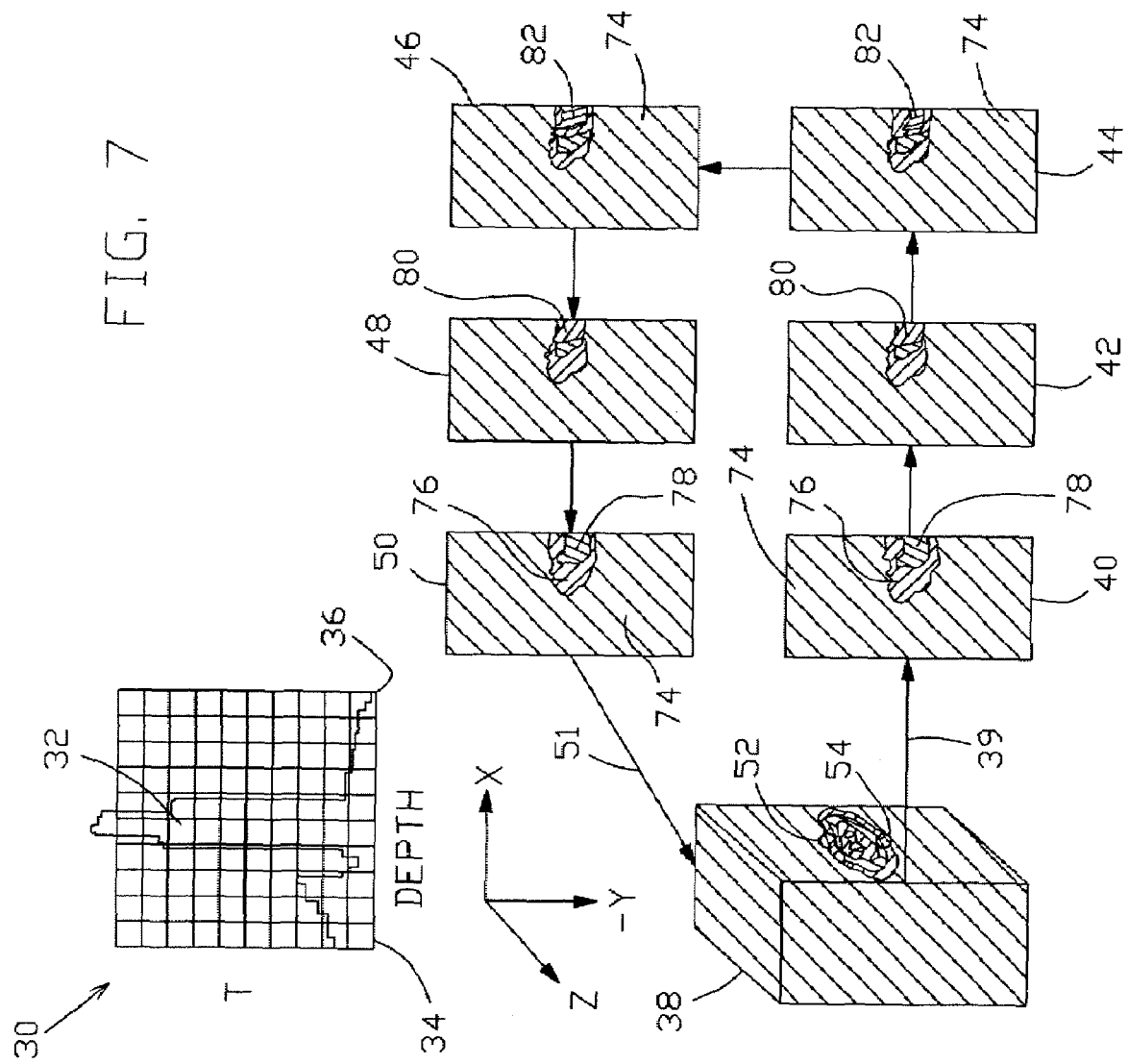
FIG. 7 is a three dimensional depiction of an isothermal profile in tissue produced utilizing a separated antenna array in accord with another embodiment of the invention without injecting saline solution into the tissue to increase conductivity of the tissue.

As an example of operation, and referring first to FIG. 1, antenna 12 in the urethra, and antenna 16 in the colon, are spaced apart by one wavelength, i.e., the frequency of the microwave power is adjusted such that the distance between urethra antenna 12 and colon antenna 16 is equal to one wavelength of the microwave signal to be transmitted by both antennas. One of the antennas is fed 180 degrees out of phase with the other. The frequency of operation is 2.5 gigahertz. As shown in FIG. 7, graph 30 shows the temperature variation versus distance between the two antennas. Urethra antenna 12 is referenced generally at position 34 as indicated in graph 30 and colon antenna 16 is referenced generally at position 36 in graph 30. In graph 30, a fairly uniform 22 degrees Centigrade temperature rise is produced in heated region 32, which is about 2 mm wide. This raised temperature is sufficient for ablating tissue and can be achieved between the two antennas without significant collateral heating, i.e., reduced or no tissue damage, of the colon wall tissue or the urethra. In this simulation, the tissue temperature adjacent both urethra antenna 12 and colon antenna 16 is approximately 36–38 degrees Centigrade, or at normal body temperature. In fact, along the distance between the two antennas, the temperature rises only six degrees centigrade, except for sharply defined region 32. Note that various types of antenna cooling could be utilized that might lower and/or further regulate these temperatures adjacent the antennas, if desired, to avoid any damage to tissues that are desired to be protected, e.g., the colon and urethra. Simulation data shows that only 5.5 watts per antenna would be required. Laboratory results corroborate the power per antenna needed. The heating time to produce this heat profile was twelve minutes. As discussed hereinbefore, the heated region 32 could be moved as desired by varying the phase difference, or other means, and therefore could be utilized for heating larger regions, if desired, such as by stepping or sweeping computer control.

Minimizing the heat generated by microwave transmission in close proximity to the antennas is a significant advantage of using multiple antennas. The microwave field levels near the antennas may be controlled to react with a destructive manner (the fields from the two antennas tend to reduce or cancel each other) while the fields between the antennas, such as region 32, may be controlled to reinforce each other in a constructive manner. The antennas would probably preferably be cooled with either running water or a phase change material or other suitable cooling means to provide additional protection and prevent any damage to the urethra and the colon.

In more detail, FIG. 7 shows isothermal zones or a heating profile produced by the antennas in cube 38. Cube 38, which is a section of the heated area, is about 48 cubic centimeters in volume. To provide more three-dimensional information on the thermal profiles, the isothermal zones are also shown on slices of cube 38 along the z-axis. Slices 40, 42, 44, 46, 48, and 50 represent sections of cube 38 from one side of cube 38 as indicated by arrow 39 to the opposite side of cube 38 as indicated by arrow 51. Urethra antenna 12 and colon antenna 16 are positioned generally as indicated in cube 38 at positions 52 and 54.

The isothermal zones of temperature created by microwave heating are indicated by the respective types of shading. In FIG. 3–FIG. 7, the outermost thermal shading zone 74 represents tissue that is heated such that the temperature change is less than five degrees centigrade. Thermal shading zone 76 represents tissue that is heated such that the temperature change is more than five degrees centigrade but less than ten degrees centigrade. Thermal shading zone 78 represents tissue that is heated such that the temperature change is more than ten degrees centigrade but less than fifteen degrees centigrade. Thermal shading zone 80 represents tissue that is heated such that the temperature change is more than fifteen degrees centigrade but less than twenty degrees centigrade. Thermal shading zone 82 represents tissue that is heated such that the temperature change is more than twenty degrees centigrade. For viewing purposes, such as for projecting the results prior to treatment using a computer simulation as discussed herein, for convenience of the user, the isothermal zones of temperature could more easily be presented in different colors rather than black and white shading.

The exact temperature at which tissue is ablated or necrosed will vary depending on various factors. The length of time the tissue remains at an elevated temperature and the maximum temperature are important factors. For relatively short periods of time, tissue heated above twenty degrees centigrade is highly likely to be necrosed. In FIG. 7, it can be seen that a significant or high percentage of the volume of tissue in thermal shading zone 82 will be necrosed due to higher temperature. Looking at the slices 44 and 46 of FIG. 7 and the associated temperature versus heating depth graph 30, it can be seen that the region of tissue to be heated is well defined. After ablation due to temperature, as the tissue dies and is reabsorbed by the body, then relief may be obtained from the benign prostatic hyperplasia condition. Tissue in thermal shading zones 80 will also likely be necrosed.

As shown in graph 30, the tissue immediately surrounding urethra antenna 12 and colon antenna 16 out to about eight millimeters is substantially unaffected by the heating, especially for relatively short heating times of a few minutes. The microwave antennas may preferably be directional antennas so that heating is very limited except in the desired directions. It will be appreciated from the above that the temperature profile can be controlled to a great extent and so can made to match a desired pattern. Moreover, the expected response can be tested for numerous variations and particular situations using the computer simulation of the present invention, as discussed hereinafter.

Additional details related to Example 2 include a heating time of twelve minutes to achieve the heating profile described in FIG. 7. Thus, the heating time for the microwave treatment of the present invention for ablation of prostatic tissue is relatively short. The total wattage absorbed after 12 minutes is 3. The wattage per antenna is 5.5. Nine cubit centimeters have a temperature greater than ten degrees Centigrade. The net joules added to the tissue while cooling the probe to 37 degrees Centigrade was 3226. The permittivity of tissue is 35. The signal absorption rate is 1.76 decibels per centimeter. The conductivity of the tissue is 0.625 S/m which may be a typical tissue conductivity. The conductivity factor is varied by differing amounts in examples 4–7 discussed hereinafter.

EXAMPLE 3

Figure 3:
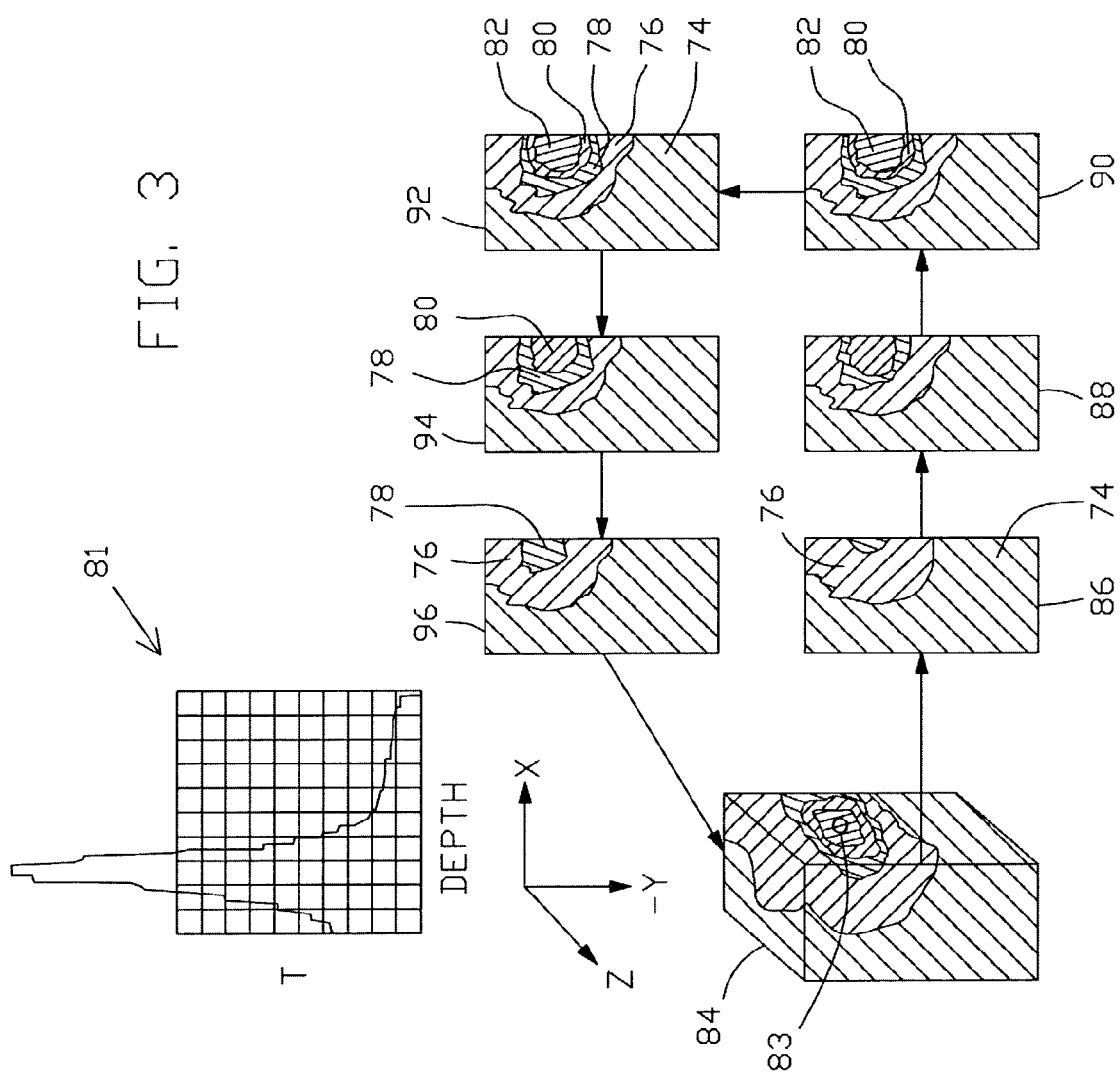
FIG. 3 is a three dimensional depiction of an isothermal profile produced utilizing a single antenna for comparison purposes with isothermal profiles as shown in FIG. 4–FIG. 7 that were produced utilizing separated antenna arrays in accord with the present invention.

The basic advantages of multiple antennas over one antenna can be seen in comparing the results discussed in Examples 1 and 2 with the heating profile shown in FIG. 3. Because there is no cooling of the antenna, the maximum temperature increase is produced around the antenna as indicated at 83 in cube 84. As per graph 81, one antenna radiates with the maximum heat generated near the antenna. The heat falls off with the depth into the tissue. This also increases the cooling problem. Note that no cooling is applied to the antenna. By using suitable cooling and other means as taught in the parent cases to this application even with only one antenna, the tissues such as the urethra and/or colon tissues could be protected in the region surrounding the antenna to provide a useful heating profile for ablating some tissue and protecting tissue surrounding the antenna. As indicated in temperature versus depth graph 81, the maximum temperature increase is 34 degrees Centigrade. The shading numbers 74–82, as described above, are used to indicate the temperature ranges found in slices 86, 88, 90, 92, 94, and 96 of FIG. 3.

The frequency of operation is 1.5 gigahertz. The heating time, as in Example 2, is 12 minutes. The volume of tissue that experiences a temperature increase of over ten degrees is 54 cubic centimeters. Other details include that the conductivity of the tissue is assumed to be 0.375 mhos/meter. The tissue permittivity is 36. The joules of energy added to the tissue are 13,788. The total watts absorbed after 12 minutes is 19.

Note that if the single antenna is inserted into a hole in the prostate as per another embodiment of the invention whereby the tissue surrounding the antenna is to be ablated, then this single antenna would be quite effective for this purpose even at lower wattage levels.

EXAMPLE 4

Figure 4:
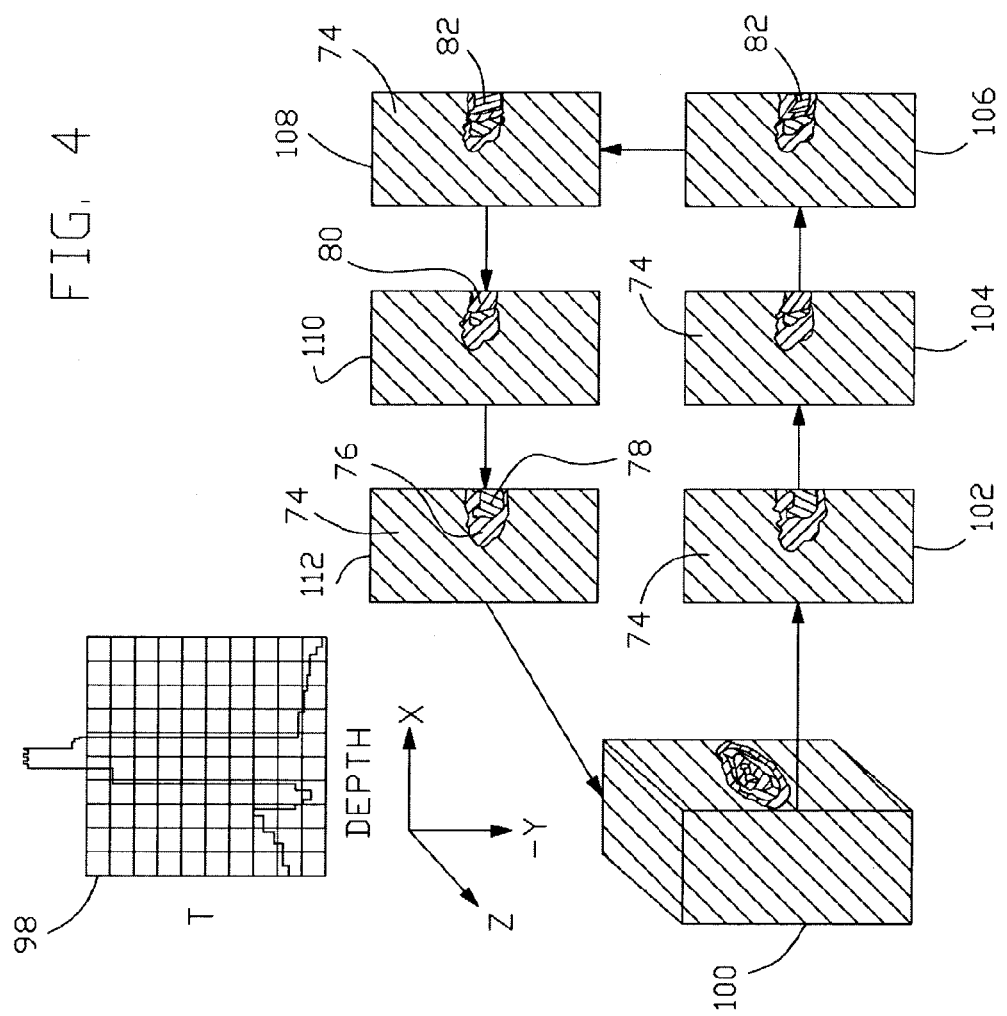
FIG. 4 is a three dimensional depiction of an isothermal profile for comparison with the isothermal profile of FIG. 7 whereby in producing the profile shown in FIG. 4 a saline solution is injected to increase conductivity in the heated tissue by a factor of two in accord with another embodiment of the invention.
Figure 5:
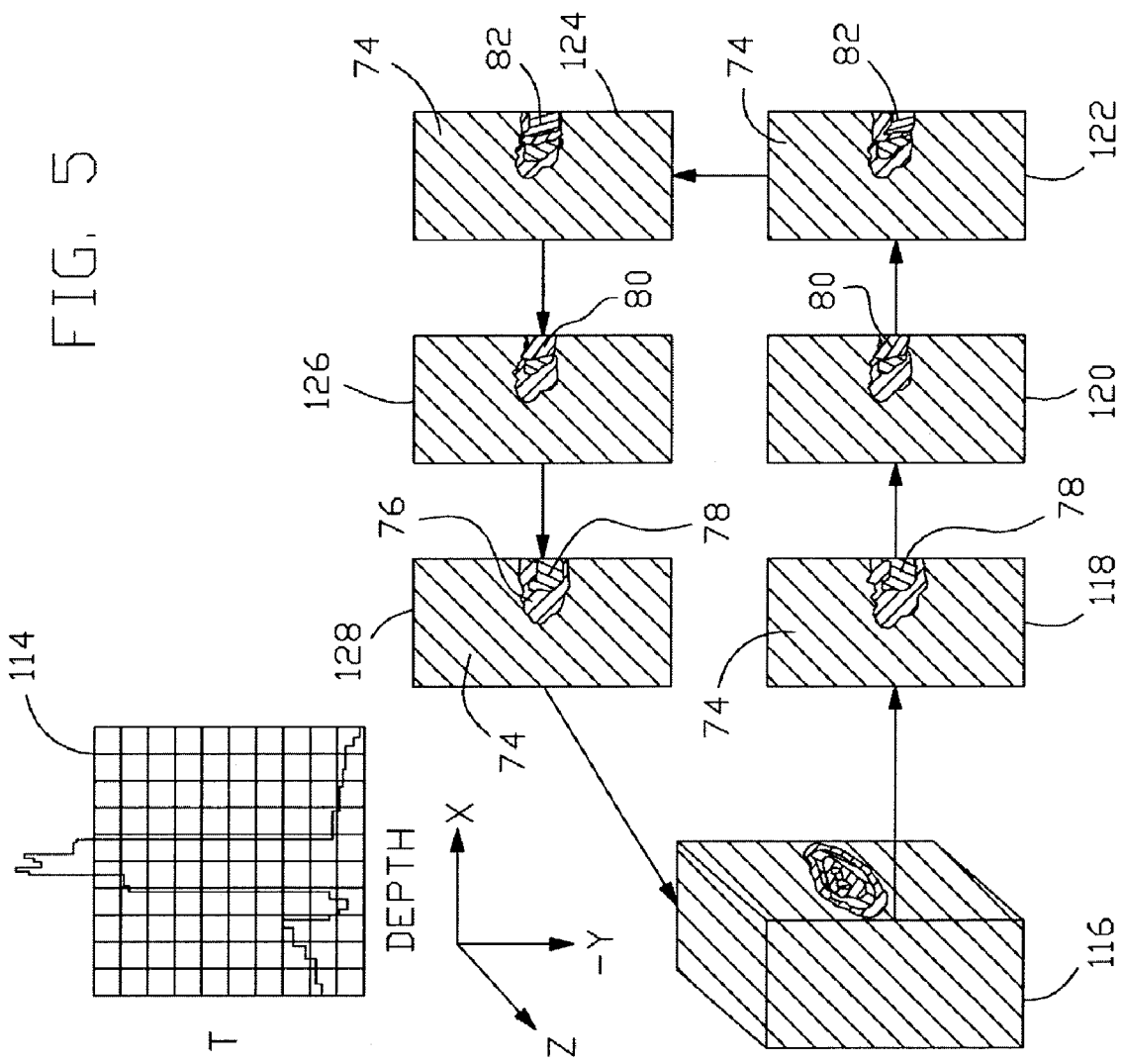
FIG. 5 is a three dimensional depiction of an isothermal profile for comparison with the isothermal profile of FIG. 7 whereby in producing the profile shown in FIG. 5 a saline solution is injected to increase conductivity in the heated tissue by a factor of four in accord with another embodiment of the invention.
Figure 6:
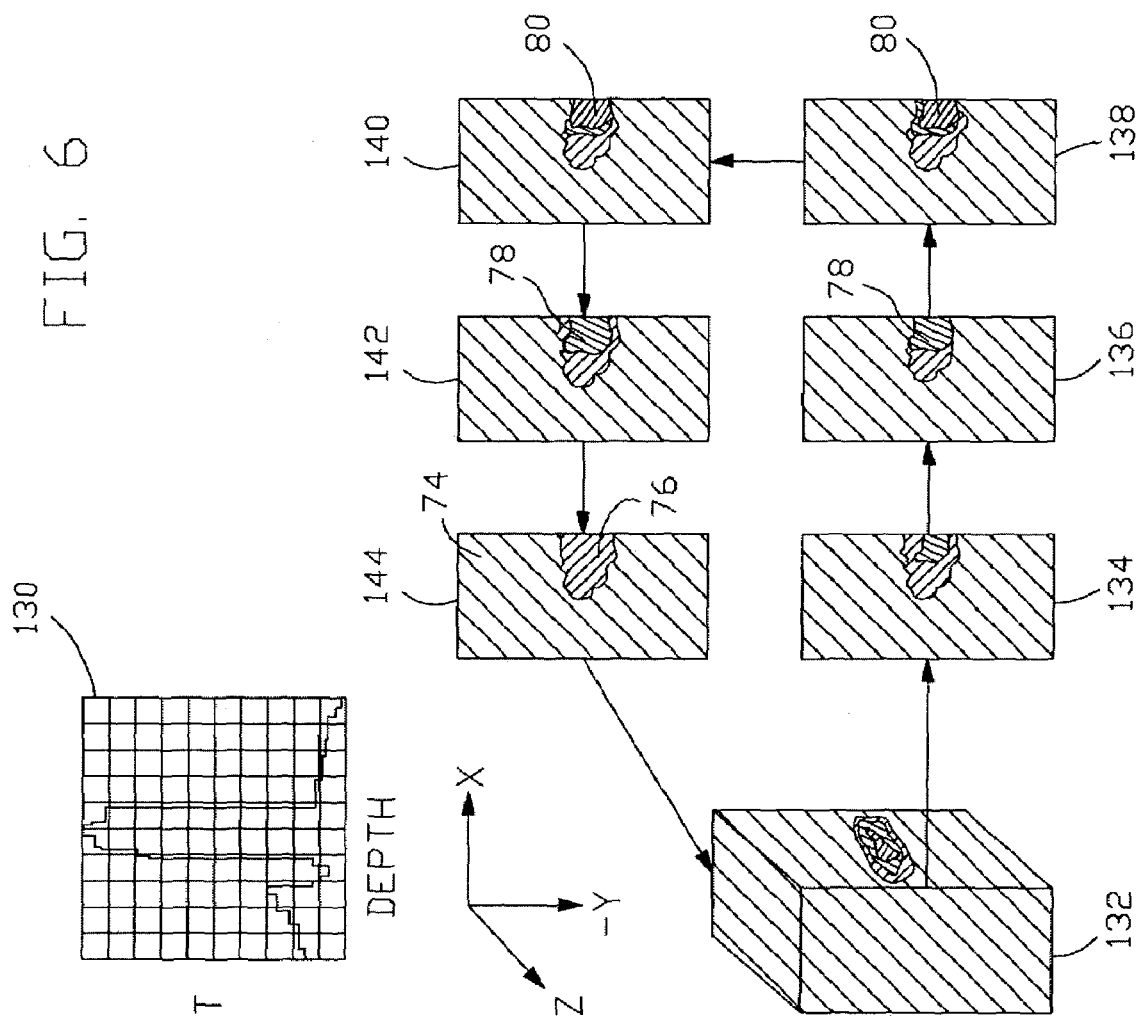
FIG. 6 is a three dimensional depiction of an isothermal profile for comparison with the isothermal profile of FIG. 7 whereby in producing the profile shown in FIG. 6 a saline solution is injected to increase conductivity in the heated tissue by a factor of eight in accord with another embodiment of the invention.

In Example 4, the results of which are shown in FIG. 4, the conductivity of the tissue to be heated is doubled, such as by saline injection, as compared to tissue conductivity for Example 2. Thus, in Example 4, the conductivity of the tissue is 1.25 mhos/meter. By injecting a saline solution (or its equivalent) into the region to be heated, the heating profile can be further enhanced. This injection increases the conductivity of the body tissue and hence increases the microwave losses, thereby generating more heat and increasing the temperature. Tests have indicated that an optimum increase in conductivity exists above which increases in temperature are limited and may even be decreased. If the conductivity is increased too much, the microwave energy has too much loss and cannot penetrate the desired heating region. The effects of changes of conductivity of the tissue are shown in FIG. 4, FIG. 5, and FIG. 6 as compared to that of FIG. 7, i.e., Example 2 in which a typical conductivity of the tissue is utilized without the use of saline injections to increase tissue conductivity. The conductivity increase produced in Example 4 by injecting saline solution into the tissue results in the heating profile as shown in FIG. 4. The conductivity of the desired heated region has been increased by a factor of two, resulting in a temperature increase of 26 degrees as best shown in temperature versus depth graph 98, while keeping other factors essentially the same as that of Example 2. The phase difference between urethra antenna 12 and colon antenna 16 is 180 degrees. The wattage for each antenna is 5.6. The total wattage absorbed during twelve minutes of heating was 3.1. The volume of tissue having an increase in temperature over 10 degrees Centigrade is 9 cubic centimeters. The number of net joules added with probe cooling was 3,281 where the antennas were cooled to 37 degrees Centigrade.

More generally, the heating profile ranges are indicated in cube 100 which in further detail is shown in slices along the z-axis by slices 102, 104, 106, 108, 110, and 112. The shading numbers 74–82, as described above, are used to indicate the same temperature ranges as discussed hereinbefore.

The increased conductivity results in about a 25% increase in the maximum temperature obtained. On the other hand, the areas of collateral heating, or heating in protected tissue regions, is virtually unaffected by the change in conductivity. Thus, the use of the change in conductivity of the tissue can be used to further sharpen the definition of the heating profile. To a certain extent, the injection of saline solution to increase conductivity may be localized so as to further sharpen or focus the microwave heating energy on the particular region to be heated as compared to the tissues to be protected.

EXAMPLE 5

In Example 5, the conductivity increased by 4 giving a maximum temperature increase of 25 degrees as best shown in temperature vs. depth graph 114 of FIG. 5. Thus, in Example 4, the temperature increase produced from quadrupling the tissue conductivity is slightly less than when the conductivity was doubled as per Example 3. Again, the collateral heating was virtually unaffected. The heating profiles shown in cube section 116 and z-axis slices 118, 120, 122, 124, 126, and 128 are similar to that of Example 3-shown in FIG. 4.

The tissue conductivity is 2.5 mhos/meter. The antenna frequency is 2.5 gigahertz. The signal absorption rate is 1.7 dB/centimeter. The phase difference between urethral antenna 12 and colon antenna 16 is 180 degrees. The wattage for each antenna is 5.6 and 3.1 watts are absorbed during the 12 minutes of heating that produce the profiles shown in FIG. 5. The volume of tissue with a temperature increase above 10 degrees Celsius is 9 cubic centimeters. The net joules absorbed, taking into account antenna cooling to keep the antennas at 37 degrees Centigrade, is 3,251.

EXAMPLE 6

In Example 6, the tissue conductivity is increased by a factor of 8 to thereby provide the tissue with a conductivity of 5 mhos/meter. The resulting temperature profiles are shown in FIG. 6, where it will be noticed that the maximum temperature increase is actually less than when no tissue conductivity increase is provided as per Example 2 shown in FIG. 7. The temperature increase for Example 6, as best shown in temperature vs. depth graph 130 is only 18 degrees Centigrade. In some cases, therefore, it may be desirable to greatly increase the conductivity of regions to be protected.

The temperature profiles provided in Example 6 are shown by temperature ranges in cube 132 which is further broken down into z-axis slices 134, 136, 138, 140, 142, and 144.

EXAMPLE 7

Figure 8:
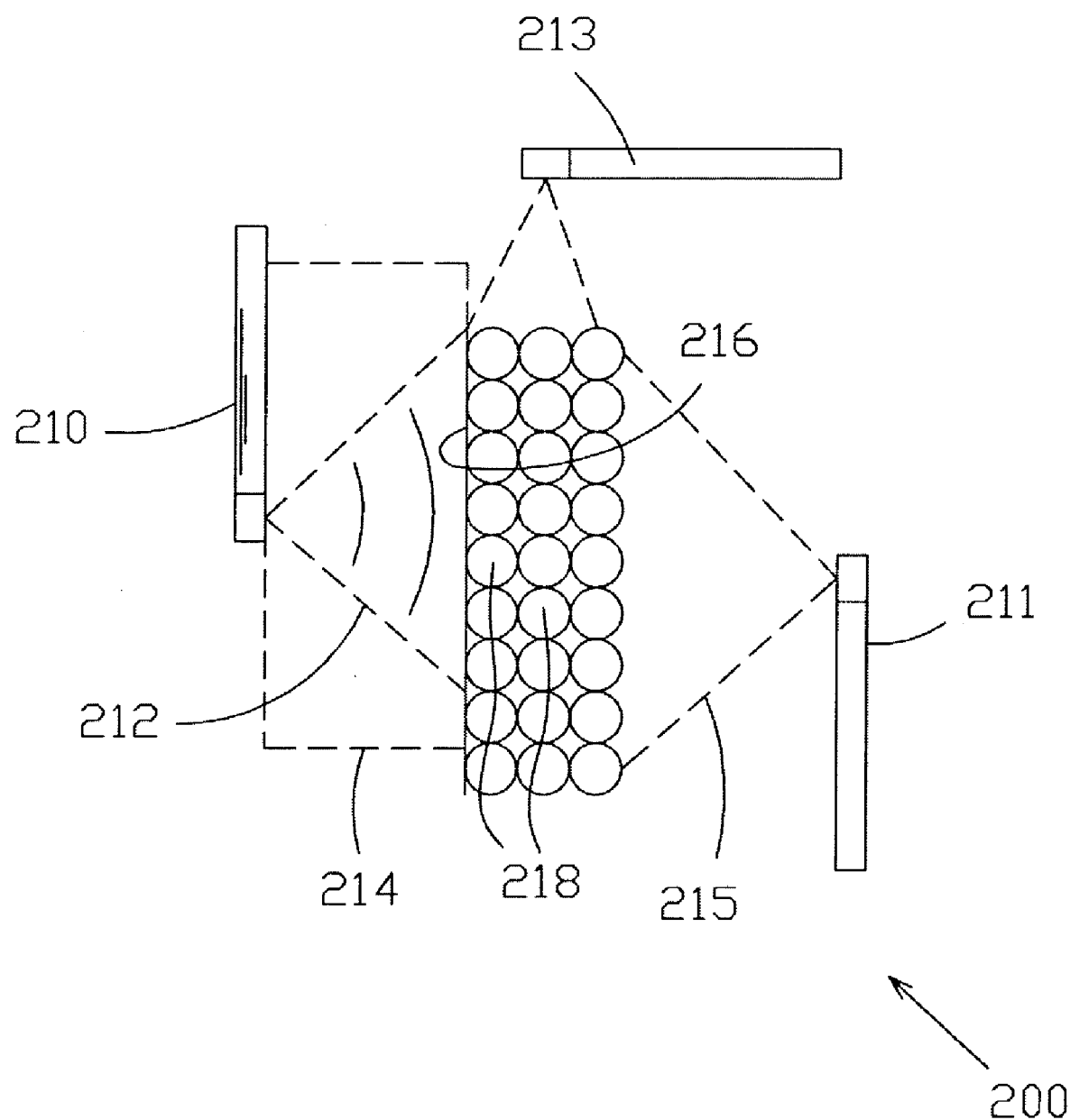
FIG. 8 describes a computer program simulation for use of a separated antenna array for predicting or controlling constructive and destructive waveform interference of a separated antenna array to produce a desired heating profile.

FIG. 8 shows the general design of simulation elements for a microwave radiator system, such as computer simulated system 200, which incorporates elements of the computer simulated system taught in the parent case to this application. The computer simulation has been written to determine the temperature profiles that can be provided in the prostate tissue. The simulation is performed by an accordingly programmed computer in which the program may be stored within a storage medium such as a hard disk or diskette. The computer effectively acts as a simulator in accord with the programming that may be contained in a memory. The inputs to the program include antenna characteristics, tissue characteristics, the frequency, power level, and delivery time of the microwave energy. A temperature profile may be produced as discussed above that shows temperature versus distance radially or orthogonally outwardly from one or more catheters or antennas. Temperature variations may also be displayed over a selected period of time.

Simulated catheter antennas 210, 211, and 213, or more or few antennas, generate microwave radiation that travels through various mediums. Although the simulation of the present invention may be used for simulating microwave energy radiation into prostate tissue, it will be apparent that other uses are also available. The antenna will have various characteristics, some of which are discussed in more detail in the parent to this application. In this embodiment, simulated fusion material or other antenna cooling means 214 may preferably form an outer layer of one or more antennas 210, 211, and 213, and, when used, may represent the first medium through which the microwave energy must travel. In a preferred embodiment, simulated fusion material layer 214 may be transparent to microwave radiation. To maintain urethral and/or colon cooling, fusion material 214 is in preferably in direct contact with tissue 216.

In the simulation, the microwave energy travels through tissue 216 and heats selected volume elements of simulated tissue referred to as computation cells 218. Each computation cell 218 may be arbitrarily selected to be one or two cubic millimeters in size in the presently preferred embodiment of the simulation although this size may be varied. The energy applied to these cells by microwave radiation is determined for each selected time increment. As well, the computer computes the energy that leaves/arrives each computation cell 218 due to thermal conduction for each computation cell 218 for each selected time increment. In this manner, a computer simulation can determine the temperature profile for the tissue over a total desired heating duration. The total desired heating duration would typically consist of a plurality of short time increments.

The inputs to the simulation include, for instance, the conductivity and relative permittivity of the prostate tissues at higher frequencies. Conductivity is especially important since the conductivity primarily determines the rate of absorption of the microwave energy into the tissue and the maximum propagation distance through the tissue.

In a presently preferred embodiment of the simulation, a computational tissue cube having a size that correlates to a region of tissue to be ablated is given the electrical and thermal characteristics of in-vivo prostatic tissue. The cube may be is subdivided into 8000 small cubes with each cube being a computational cell such as computation cell 118. The instantaneous heat of one arbitrary computational cell in the cube is given by:

$$Q_C = Q_C^\circ + \left(\Delta Q_{RF} + \int \Delta Q_{HC}\right)\Delta t$$

where:

$Q$ is the new heat energy in the computational cell;

$Q_C^\circ$ is the previous heat energy level;

$\Delta Q_{RF}$ is the heat added due to absorption of microwave energy;

$\int \Delta Q_{HC}$ is the net heat added or lost by the cell from heat conduction; and $\Delta t$ is a small time constant.

The new temperature of the cell is given by:

$$T_C = Q_C / MS$$

where:

$T_C$ is the new cell temperature in °C.;

$M$ is the mass of the cell; and $S$ is the specific heat of the cell.

Each cell is assumed to be a cube with six faces. The heat energy transferred through each face for one time increment is given by:

$$\Delta Q = -KA(\partial T / \partial r)\Delta t$$

where:

$\Delta Q$ is the heat transferred through one face;

$K$ is the thermal conductivity of the cell;

$\partial T / \partial r$ is the temperature gradient from the center of one cube to the next; and $A$ is the area of one face.

For each antenna, the electric field intensity in a cell is given by:

$$\hat{E} = \frac{\hat{E}_{01} e^{-\gamma r_1}}{r}$$

where:

$\hat{E}_1$ is the electric field intensity resulting from the radiation at the feed point of the one or more antennas;

$\hat{E}_{01}$ is related to the relative magnitude and phase of radiation from the feed point of the antennas;

$\gamma = \alpha + j\beta$;

$\alpha$ is the attenuation constant associated with the tissue;

$\beta$ is the phase shift constant; and $r_1$ is the distance from each antenna feed point to the center of a cell.

While various types of antennas may be used, an disk loaded antenna with two disks and a feed point, as taught in the parent cases to this application, have a total electric field at a cell due to radiation from the feed points for each antenna feed point, middle disk and top disk (each being a microwave radiator) that is given by:

$$\hat{E} = \hat{E}_1 + \hat{E}_2 + \hat{E}_3$$

where:

$\hat{E}_2$ is calculated similarly to $\hat{E}_1$ except using $r_2$ from the mid-disk; and $\hat{E}_3$ similarly using the top disk associated $r_3$.

The computer determines the effect of destructive and constructive interference of the waveforms to determine the total electric field of all antennas.

Finally, the energy absorption at the cell for all antennas is given by:

$$W_a = vo'|E|^2 dt$$

where:

$W_a$ is the electromagnetic energy absorbed;

$v$ is the volume of the cube; and $o'$ is the conductivity of the medium.

The results from the simulation can be plotted in numerous ways such as those disclosed above. As well, given a particular desired profile the necessary input characteristics can be obtained such as power levels, operating time and frequency. Thus, the simulation can be used to determine results from particular inputs or to calculate the necessary inputs to obtain desired results.

In operation of the present invention, a computer simulation may be used to determine to predict what the temperature profile will be in the prostatic tissue. The temperature profile can be modified until it appears to fit the desired result. The amount of tissue to be necrosed can be calculated. If two antennas are used as shown in FIG. 1, then catheter 10 and urethral antenna 12 are then positioned in the urethra at the desired position at which prostatic tissue is to be selectively removed with respect to catheter 14 and colon antenna 16. The microwave antennas 14 and 16 are turned on at the predetermined power level for the predetermined heating time. The urethra is undamaged due to antenna cooling and/or the addition/subtraction of microwave radiation as discussed hereinbefore. In the next several weeks, the body reabsorbs necrosed tissue thereby providing relief to the patient of benign prostatic hyperplasia symptoms.

In another more invasive method for heating selected areas of the prostate, one or more catheters may be inserted directly into the prostate. This would be accomplished by creating small diameter holes in the prostate (7 French). Cooling may not be required for this technique since it is not necessary to preserve he tissue immediately adjacent to the radiators.

In general, for the present invention, the desired frequency range of operation of the microwave antennas would be between 600 MHz and 4000 MHz depending upon the desired spatial location and separation of the antennas.

There are many possible variations of the present invention that provide great flexibility of operation for the specific requirements of use. One antenna may be utilized in the urethra, or a plurality of catheters, depending on the size, may be utilized with several antennas mounted thereto. Thus, one urethral antenna or multiple urethral antennas may be utilized by themselves or in conjunction with other antennas such as antennas positioned in the colon. Likewise, one or multiple colon antennas and/or multiple colon catheters may be utilized to operate by themselves or in conjunction with one or more urethral antennas. Moreover, laparoscopy techniques may be utilized to position one or more additional antennas wherever desired in the body and for purposes used herein a catheter is considered equivalent to laparoscopic insertion tubes or any other member such as a flexible member insertable into the body. Thus, such one or more antennas may be utilized to apply heat to other body tissues, such as heart tissues, or other organ tissues, as desired. The antennas may be cooled by flowing cooling fluid, such as water, or by using the heat of fusion of a phase change material. The conductivity of the desired heated region may be altered as discussed above to accelerate microwave absorption and heating, as desired. It may be desired to have different conductivity saline solutions in different tissues or surrounding tissues as desired to either promote or discourage heating. Any antenna inserted into the body by any means may be referred to herein as a transcatheter antenna. Tissues may refer to any body components or elements.

Thus, while the preferred embodiment of the catheter apparatus and methods are disclosed in accord with the law requiring disclosure of the presently preferred embodiment of the invention, it is clear from the above descriptions that other embodiments of the disclosed concepts may also be used. Therefore, the foregoing disclosure and description of the invention are illustrative and explanatory thereof, and various changes in the method steps and also the details of the apparatus may be made within the scope of the appended claims without departing from the spirit of the invention.

What is claimed is:

1. A method for producing a selected heating profile in a tissue region of a body, comprising:
    positioning a first microwave antenna adjacent said tissue region;
    positioning a second microwave antenna adjacent said tissue region;
    controlling said first microwave antenna and said second microwave antenna to produce a desired heating profile in said tissue region by utilizing constructive and destructive interference of microwave transmissions from said first microwave antenna and said second microwave antenna;
    inserting said first microwave antenna into a urethra of said body; and
    inserting said second microwave antenna into a colon of said body such that at least a portion of a prostate of said body is substantially between said first microwave antenna and said second microwave antenna.

2. The method of claim 1, further comprising:
    varying the conductivity of said tissue region.

3. A method for selective thermal ablation of a tissue to be treated while limiting thermal damage to a protected tissue, comprising:
    positioning at least two energy radiators adjacent to said tissue to be treated and said protected tissue; and
    controlling energy radiation from said at least two energy radiators to produce a thermal profile such that constructive interference of said energy radiation produces a temperature increase in said tissue to be treated for thermal ablation thereof and destructive interference of said energy radiation limits thermal damage to said protected tissue;
    positioning a first energy radiator adjacent a prostate at a first position, and positioning a second energy radiator adjacent said prostrate at a second position; and
    wherein said first energy radiator is positioned within a urethra and said second energy radiator is positioned within a colon.

4. A process of operating a general purpose computer of known type comprising a data processor to enable said data processor to execute an object program comprising a plurality of formulas for determining a temperature profile in a biological tissue due to microwave radiation, comprising the steps of:
    providing position information for a plurality of microwave antennas with respect to each other and with respect to said biological tissue;
    providing at least one frequency of operation for said plurality of microwave antennas;
    providing a phase difference of said microwave radiation for said plurality of microwave antennas;
    modeling said biological tissue as a plurality of three-dimensional cells;
    determining heat flow into each of said plurality of three-dimensional cells as a result of at least said microwave radiation;

determining heat flow out of each of said plurality of three-dimensional cells as a result of at least heat convection; and calculating an accumulated temperature change in each of said plurality of three-dimensional cells as a result of said accumulated heat flow into and said accumulated heat flow out of each of said plurality of three-dimensional cells.

5. The process of claim 4, further comprising:

providing a power level of operation of said plurality of microwave antennas.

6. The process of claim 4, further comprising:

inputting conductivity of said biological tissue.

7. The process of claim 4, further comprising:

providing a delivery time of microwave energy.

8. The process of claim 4, further comprising:

determining an effect of cooling applied adjacent said plurality of antennas.

* * * * *